(12) United States Patent
Kuhn et al.

(10) Patent No.: US 8,720,276 B2
(45) Date of Patent: *May 13, 2014

(54) MOMENT FRACTION COMPUTATION FOR SENSORS

(75) Inventors: Jonathan L. Kuhn, Ham Lake, MN (US); Jonathan P. Roberts, Coon Rapids, MN (US); James D. Reinke, Maple Grove, MN (US); Richard J. O'Brien, Hugo, MN (US); Michael B. Terry, Camas, WA (US); Kamal Deep Mothilal, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 335 days.

This patent is subject to a terminal disclaimer.

(21) Appl. No.: 13/176,018

(22) Filed: Jul. 5, 2011

(65) Prior Publication Data

US 2012/0245489 A1 Sep. 27, 2012

Related U.S. Application Data

(60) Provisional application No. 61/467,172, filed on Mar. 24, 2011.

(51) Int. Cl.
*G01L 7/00* (2006.01)

(52) U.S. Cl.
USPC .......................................................... 73/700

(58) Field of Classification Search
None
See application file for complete search history.

(56) References Cited

U.S. PATENT DOCUMENTS

| | | | |
|---|---|---|---|
| 4,911,016 A | 3/1990 | Miyazaki |
| 5,167,158 A | 12/1992 | Kamachi |
| 5,535,752 A | 7/1996 | Halperin |
| 5,564,434 A | 10/1996 | Halperin |
| 7,013,178 B2 | 3/2006 | Reinke |
| 7,139,613 B2 | 11/2006 | Reinke |
| 7,284,441 B2 | 10/2007 | Zdeblick |
| 7,398,688 B2 | 7/2008 | Zdeblick |
| 7,623,053 B2 | 11/2009 | Terry |
| 7,714,757 B2 | 5/2010 | Denison |
| 2002/0056324 A1 | 5/2002 | Penzar et al. |
| 2009/0167327 A1 | 7/2009 | Harish |

OTHER PUBLICATIONS (PCT/US2012/030302) PCT Notification of Transmittal of the International Search Report and the Written Opinion of the International Searching Authority, Mailed Jul. 2, 2012, 9 pages.
(PCT/US2012/030293) PCT Notification of Transmittal of the International Search Report and the Written Opinion of the International Searching Authority, Mailed Jul. 5, 2012, 13 pages.

*Primary Examiner* — Andre Allen
(74) *Attorney, Agent, or Firm* — Evans M. Mburu

(57) ABSTRACT

An implantable medical sensor system provides signals representative of a magnitude of moment fraction applied to a sensor module at a selected site. A sensor module includes a first transducer producing a first signal having an associated first response to pressure and strain applied to the sensor module and a second transducer producing a second signal having an associated second response to pressure and strain applied to the sensor module. A moment fraction is computed in response to the first signal and the second signal. In various embodiments, the moment fraction is used to guide positioning of the sensor module, indicate a need for repositioning the sensor module, report loading of the sensor module during normal operation for use as sensor design information and in setting sensor calibration ranges.

24 Claims, 9 Drawing Sheets

US 8,720,276 B2

MOMENT FRACTION COMPUTATION FOR SENSORS

CROSS REFERENCE TO RELATED APPLICATIONS

This application claims the benefit of and priority to U.S. Provisional Application Ser. No. 61/467,172, entitled "Strain Compensation for Pressure Sensors", filed Mar. 24, 2011, the contents of which are incorporated by reference herein in its entirety.

TECHNICAL FIELD

The instant disclosure relates generally to computing moment fraction applied to physical sensors.

BACKGROUND

Sensors of physical signals are typically sensitive to multiple physical influences. The art of sensor design is to ensure that the sensor is the most sensitive to a physical parameter of interest. The challenge is to isolate a sensing element of one physical phenomenon from confounding physical phenomena.

For example, sensors that are placed in an environment in which varying mechanical loads may be imposed on the sensor may be subject to strain-induced errors in a physical signal measurement. It is often desirable to measure or monitor pressure within a patient's body. Blood pressure, cranial pressure or other intracavitary or internal body pressures may be monitored for assessing a patient condition and may be used in managing or controlling medical treatment. A pressure sensor implanted in a patient's body will be subjected to temperature changes as well as movement and physical forces other than pressure. For example, motion due to the beating heart, respiration or body motion may cause bending or strain of a pressure sensor module. A sensor module may be at least partially isolated from other movement and forces by positioning the pressure in or on a stiff housing that does not bend under normal operating conditions.

A housing or sensor platform that is stiff enough to prevent flexure or strain due to imposed forces on the sensor, however, may be undesirable or poorly tolerated by a patient when incorporated in an implantable medical device (IMD). For example, in a transvenous lead for monitoring blood pressure, added stiffness to the lead may make lead advancement and navigation through a tortuous pathway along the patient's cardiovascular system difficult or impossible. The stiffness of a sensor housing implemented along an otherwise flexible lead body may cause undesired strain between the housing and flexible lead body when exposed to flexure and movement associated with a beating heart or other motion. A need remains, therefore, for a pressure sensor and associated method for compensating for bending error caused by strain applied to the pressure sensor and for determining information relating to the mechanical loading of a sensor.

DETAILED DESCRIPTION

In the following description, references are made to illustrative embodiments. It is understood that other embodiments may be utilized without departing from the scope of the disclosure.

Figure 1:
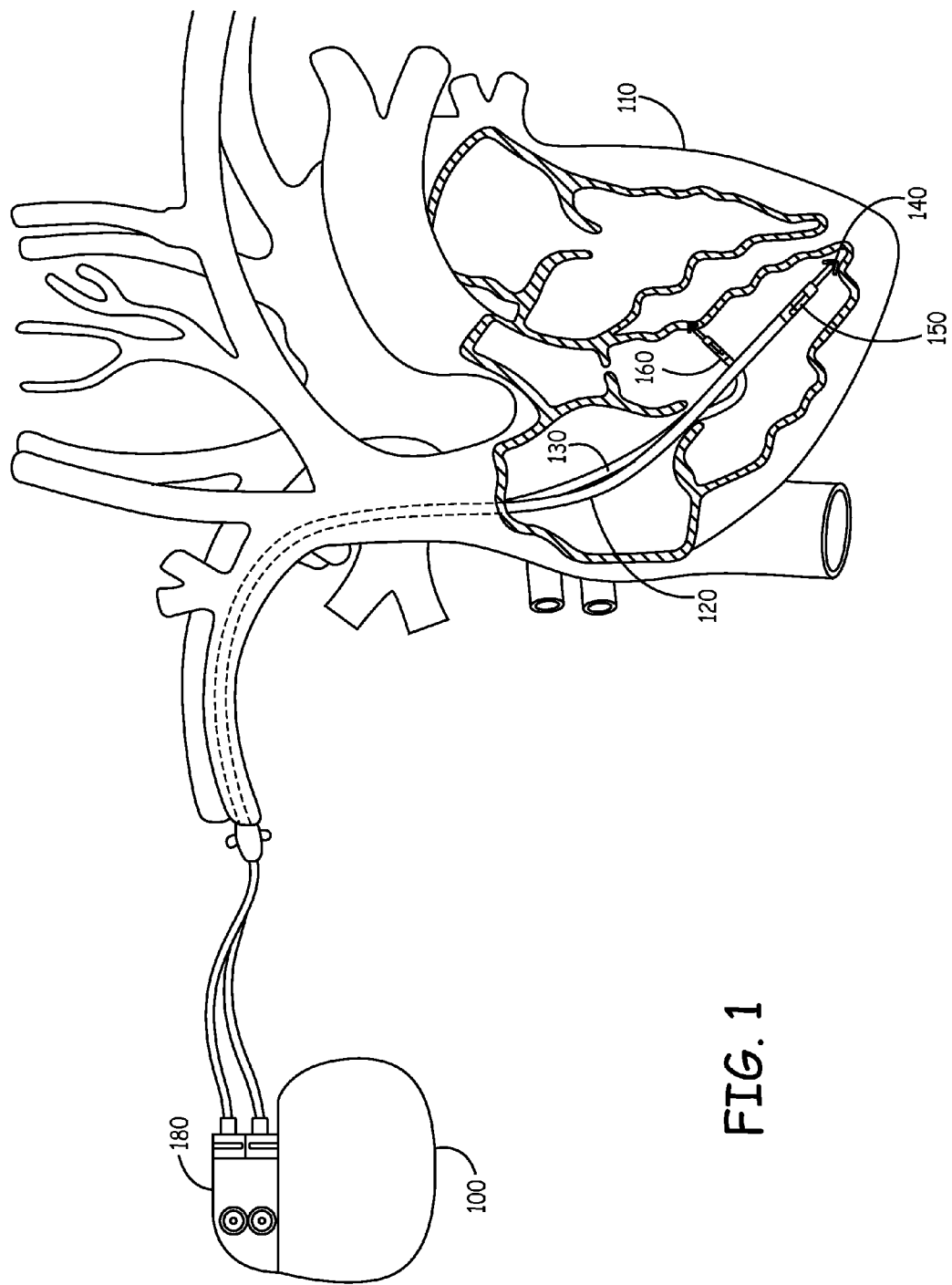
FIG. 1 is an illustration of an implantable medical device (IMD) 100 configured to monitor pressure in a patient's heart in accordance with at least one embodiment of the present disclosure.

FIG. 1 is an illustration of an implantable medical device (IMD) 100 configured to monitor a patient's heart 110 in accordance with at least one embodiment of the present disclosure. In this illustration, a human heart 110 is depicted showing two possible positions of sensing leads 120, 130 that are implanted inside the heart 110. Each sensing lead 120, 130 has a distal tine assembly 140 located at the distal end of the lead. The distal tine assembly 140 is used as an anchor to implant the distal end of the lead into the heart's chamber.

The sensing leads 120, 130 also each include a sensor module 150, 160 that is located towards the distal end of the lead. Each sensor module 150, 160 includes at least two transducers and circuitry for measuring transducer signals enclosed within a sensor module housing. The sensor modules 150, 160 provide signals that are representative of the magnitude of the absolute pressure and body temperature at the site of implantation. These signals are transmitted from the sensor modules 150, 160 to the IMD 100 via electrical conductors extending through sensing leads 120, 130, which are coupled at their proximal ends to connector block 180 of IMD 100.

The leads and sensor locations shown in FIG. 1 are intended to show possible locations and configurations of a lead carrying a sensor module. For example, sensor module 150 is positioned near the right ventricular apex whereas sensor module 160 is positioned substantially in the right ventricular outflow tract. The sensor location may vary between applications. For example, a single right ventricular sensor module may be employed to monitor pressure in the right ventricle instead of the two sensors as shown here.

In other embodiments, the system may employ more or less sensing leads than as illustrated in FIG. 1. In alternative embodiments, sensing leads 120, 130 may be placed at other locations in heart 110 than those shown in FIG. 1 or other locations along the cardiovascular system, including venous or arterial locations. In addition, in some embodiments, the system may employ leads 120, 130 that contain more than one sensing module 150, 160 per lead.

In still other embodiments, sensor modules may be implemented in a leadless design in which a deployable housing including a sensor module and telemetric communication circuitry is deployed to a body location for monitoring pressure. The wireless sensor transmits signals to IMD 100 or to an external device via wireless telemetry. Examples of implantable medical device (IMD) communication systems that may be employed by the system of the present disclosure include, but are not limited to, the systems disclosed in commonly-assigned U.S. Pat. No. 7,013,178 (Reinke et al.) and U.S. Pat. No. 7,139,613 (Reinke et al.), the disclosures of which are incorporated herein by reference in relevant parts.

In the illustrative embodiment of FIG. 1, sensor modules 150, 160 are deployed for measuring a patient's blood pressure. In alternative embodiments, a pressure sensor may be deployed in other body chambers or cavities, such as along the digestive tract, within the bladder, within the thoracic or abdominal cavity, or within or along an organ such as the brain, a muscle, etc. A pressure sensor module may be deployed for measuring a fluid pressure or measuring a pressure within or between tissues, such as an intramuscular pressure.

Figure 2:
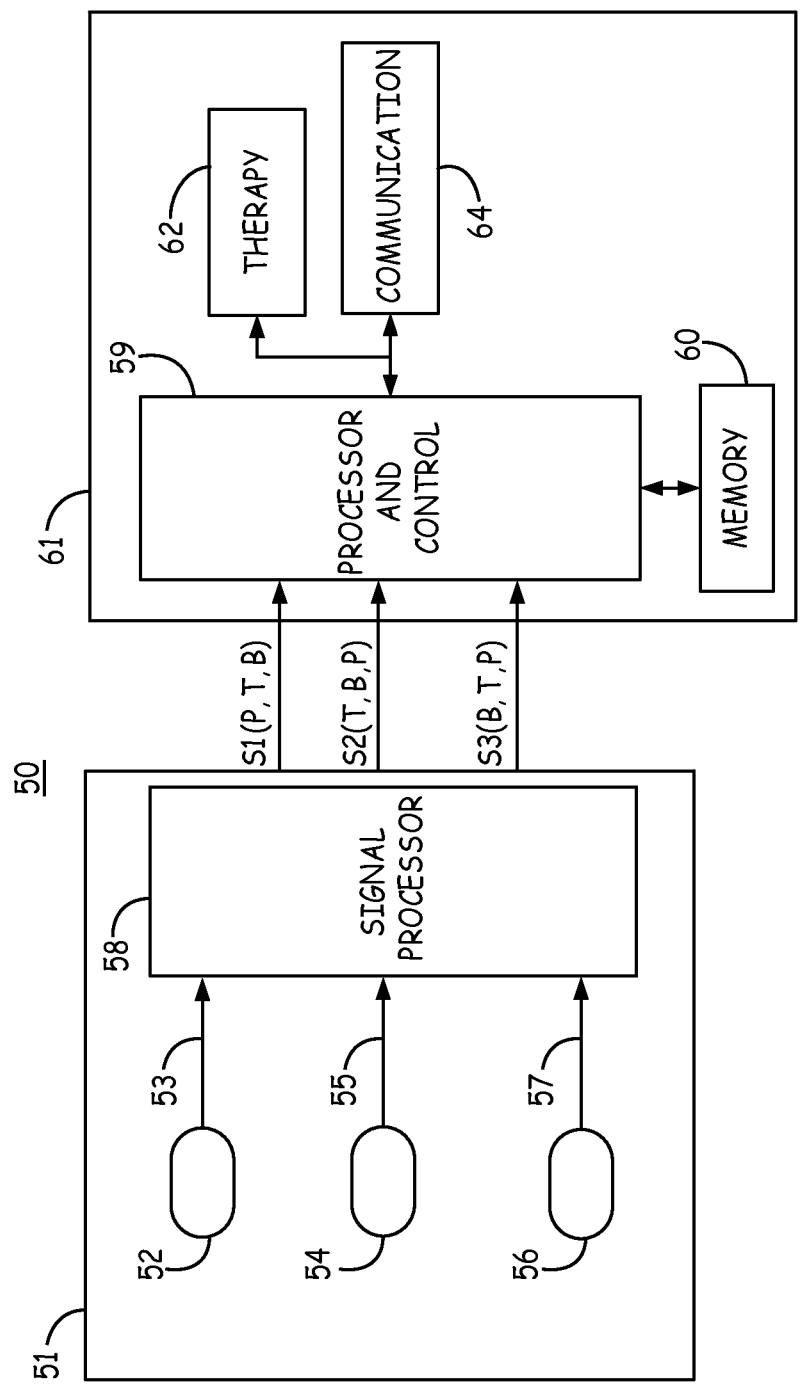
FIG. 2 is a functional block diagram of a medical device system for monitoring transducer signals and providing strain compensation of the pressure signal.

FIG. 2 is a functional block diagram 50 of a medical device system for monitoring a pressure signal and providing strain compensation of the pressure signal. A sensor module 51, which may correspond to modules 150 or 160 in FIG. 1, is coupled to an IMD 61, in either wired or wireless communication to enable signal transmission from sensor module 51 to IMD processor and control 59.

Sensor module 51 includes a pressure transducer 52 provided for producing an electrical signal output 53 correlated to the pressure imposed on a sensor module housing (not shown in FIG. 2) containing or carrying transducer 52. Pressure transducer 52 may be embodied as any pressure-sensitive transducer, including, but not limited to, piezoelectric, capacitive, electromagnetic, piezoresistive, optical, or potentiometric transducers. The pressure transducer 52 is also subject to temperature changes and strain imposed on the housing enclosing transducers 52, 54, and 56. The pressure transducer 52 produces an electrical signal 53 that varies with pressure P, temperature T and strain or bending B applied to the sensor module housing containing transducer 52. The output signal 53 of transducer 52 used alone for deriving a pressure measurement or monitoring relative changes in pressure would result in erroneous measurements due to strain-induced changes in the output signal 53 caused by bending or strain imposed on the sensor housing.

In order to compensate for strain-induced error of the pressure transducer signal 53, a second signal transducer 54 is provided which is also sensitive to strain, temperature and pressure but not with the same dependency as pressure sensor 52. Transducer 54 produces a signal 55 correlated to strain or bending imposed on the sensor housing holding transducers 52, 54 and 55, with additional dependency on temperature and pressure changes.

A third transducer 56 is included which produces an electrical output signal 57 that is sensitive to changes in temperature and pressure (and optionally strain) but with different dependencies on these variables than the first and second transducers 52 and 54. The transducers 52, 54 and 56 may be selected and configured such that signal 53 is most highly sensitive to pressure, signal 55 is most highly sensitive to strain or bend, and signal 57 is most highly sensitive to temperature. In this way, each transducer output signal 53, 55 and 57 may vary with the three variables of pressure, temperature and bending but in an independent manner that allows the three signals to be used in solving for each of the variables independently.

Signal processor 58 receives the transducer output signals 53, 55 and 57 and computes three measurement signals S1, S2 and S3 that are provided for use by processor and control 59 for computing a calculated pressure (that is not compensated for bending-induced pressure signal changes) and a bending pressure error using at least two out of the three signals. S1, S2 and S3 are derived from the transducer signals, in any combination, to obtain a measurement signal S1 that is most sensitive to pressure (but also sensitive to temperature and bending), S2 that is most sensitive to temperature (and may be sensitive to bending and pressure), and S3 that is most sensitive to bending (and may be sensitive to temperature and pressure).

The pressure measurement calculated from S1 alone will include error due to strain or bending of the sensor module. The bending pressure error is a correction term computed using an established relationship between strain on the sensor module and a difference between actual applied pressure and the calculated pressure or the measurement signal S1. Using the third transducer signal S3, which is most sensitive to bending, to compute a pressure correction term, the signal processor 58 can compute a pressure signal corrected for the influences of both temperature and strain or bending.

Signal processor 58 thus processes the transducer output signals 53, 55 and 57 to compute three measurement signals S1, S2 and S3 from which processor and control 59 can compute a pressure measurement corrected for temperature changes and for strain-induced error, also referred to herein as a bend-compensated pressure signal.

Processor and control 59 may additionally compute a temperature signal output using at least S2. In some embodiments, temperature may be controlled such that temperature changes do not influence the pressure transducer signal 53. In that case, S3 is used to compensate S1 for pressure error due to strain. In some sensor module designs, one transducer 56 is embodied as a MEMs or other sensor incorporated on a rigid portion of the sensor module and may be isolated from pressure changes such that one output signal 57 varies substantially with temperature only and is used to provide S2.

Processor and control 59 receives S1, S2, and S3 and computes a corrected pressure measurement to control a therapy delivered by therapy delivery unit 62 and/or to generate reports, data or other information that is communicated via communication unit 64. Communication unit 64 may include a telemetry communication system, display, patient alert or other functionality for communicating information or data derived from the corrected pressure signal to the patient or a clinician. Processor and control 59, memory 60 and communication unit 64 are configure to cooperatively generate notifications in response to measurements of the moment fraction applied to the sensor module 51, as will be described in detail herein. Notifications may include generating and transmitting a report of accumulated moment fraction measurements, producing or transmitting an alert relating to an out-of-range moment fraction, and flagging pressure measurements determined using an out-of range moment fraction.

Operations performed by signal processor 58 and processor and control 59 for computing a corrected pressure measurement may be implemented entirely in signal processor 58 within the sensor module 51, entirely within processor and control 59 within an IMD 61, which is communicatively coupled to sensor module 51 for receiving transducer output signals 53, 55 and 57, or in a distributed manner across processing components included in IMD system 50.

In one embodiment, a moment fraction (mf) is computed as a ratio of the bending moment applied to the sensor module to a maximum bending moment expected under normal operating conditions. This mf signal is correlated to the amount of strain applied to the sensor module and may provide useful information regarding the operating conditions of the sensor module.

Processor and control 59 may additionally receive a mf signal and may store data or other information relating to mf, which may be is communicated to an external device via communication unit 24. The mf signal may provide useful information relating to the strain the sensor module is exposed to during an implantation procedure or during operation. Such information may guide placement of the sensor, e.g. during an initial surgical implantation procedure, and/or re-positioning of the sensor to a desired monitoring site. The mf signal may also provide useful information to engineers in determining sensor module design requirements.

Figure 3:
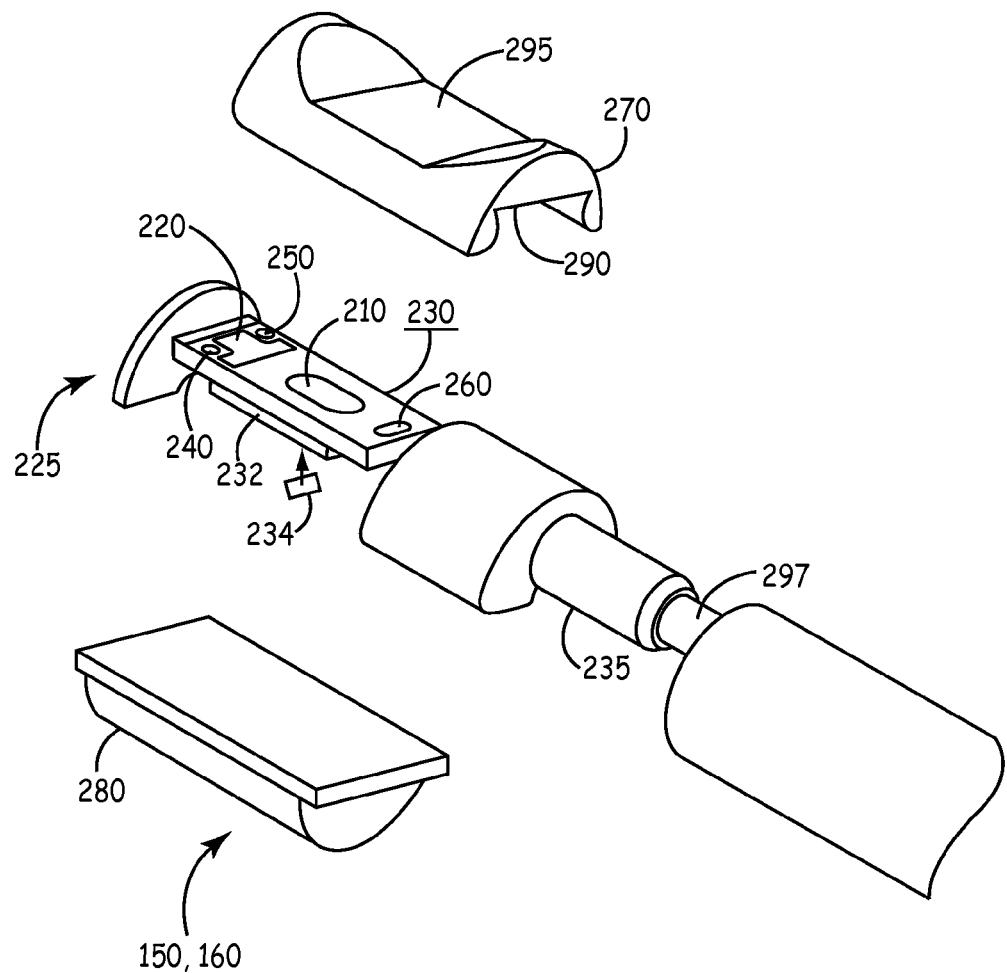
FIG. 3 contains a partial exploded perspective top view of the components of a sensor module in accordance with at least one embodiment of the present disclosure.

FIG. 3 contains a partial exploded perspective top view of the components of the sensor module 150, 160 in accordance with at least one embodiment of the present disclosure. Sensor module 150, 160 senses pressure at the site of implantation and transmits signals that are correlated to the magnitude of the absolute pressure, temperature, and externally applied static and dynamic moments at the site of implantation through a feedthrough pin 297 that is located at the proximal end 235 of the sensor module.

In this exploded view, the sensor module 150, 160 is formed with a first and second titanium cylindrical housing half member 270, 280. When the cylindrical housing half members 270, 280 are joined together, they provide an assembled titanium housing that surrounds a ceramic hybrid circuit substrate 230.

In this illustrative embodiment, sensor module 150, 160 includes a capacitive type of pressure transducer. The sensor module 150, 160 is shown to contain a first capacitive plate 210 forming an air gap pressure sensitive capacitor, also referred to herein as a "pick-off" capacitor (Cpo) and a second capacitive plate 220 forming an air gap reference capacitor (Cref). Cpo provides a signal that is sensitive to pressure, temperature, and bending of module 150, 160. The Cref plate 220 is located towards the distal end 225 of the sensor module. Cref provides a signal that is sensitive to temperature and to bending with less sensitivity to pressure than Cpo. Each capacitor plate 210, 220 is electrically coupled to a top side of substrate 230. The sensor module 150, 160 further includes three plated standoffs 240, 250, 260.

When the cylindrical housing half members 270, 280 are assembled, the capacitor plates 210, 220 are spaced from the inner surface 290 of cylindrical half housing member 270 by the height of the three standoffs 240, 250, 260. The air gap pressure sensitive capacitor Cpo varies in capacitance with the amount of pressure and moment that is imposed on the diaphragm 295 that is located on cylindrical half housing member 270. When sensor module 150, 160 is implanted in a patient's body, the temperature inside module 150, 160 can vary with body temperature, for example during fever or exercise. Temperature induced changes in pressure inside the sensor module will affect the deflection of diaphragm 295 and will therefore also cause changes in the capacitance of Cpo 210.

A measurement of temperature may be used to compensate for temperature induced changes in pressure. This can be performed in conjunction with capacitance measurements, such as disclosed in U.S. Pat. No. 5,564,434 (Halperin, et al.), hereby incorporated herein by reference in its entirety. Alternatively, temperature changes may be separate from the capacitance measurements using any temperature measurement technique.

The Cref plate 220 is located in a peripheral region of substrate 230 relative to diaphragm 295. Deflection of diaphragm 295 in the peripheral region of Cref plate 220 is substantially less than deflection of diaphragm 295 in the region of Cpo plate 210. Capacitance Cref is relatively less sensitive to changes in pressure than the capacitance Cpo. Changes in Cpo and Cref measurements, however, may introduce measurement error as changes in bending moment applied to sensor module 150, 160 occur.

The sensor module 150, 160 includes a hybrid circuit 232 on the bottom side of substrate 230. Circuit 232 includes circuitry that provides measurement signals S1, S2 and S3 as shown in FIG. 2 for processing in an algorithm that computes a corrected pressure measurement compensated for both temperature and bending moment. In one embodiment, a measurement signal S1 is a measurement of capacitances Cpo and Cref, which may correspond to transducers 52 and 54 in FIG. 2. S1 may be expressed as a ratio of these capacitances (or measurements correlated thereto) and such a ratio is referred to herein as a duty cycle, DCpo.

S2 is provided as a measurement signal that is correlated to temperature. S3 is provided as a measurement signal that is correlated to bending moment, for example a measurement of Cref and a third capacitor Coc that is relatively insensitive to bending moment, as further described below. These capacitances Cref and Coc may correspond to the output signals 55 and 57 of transducers 54 and 56, respectfully, in FIG. 2. The measurement signal S3 may be expressed as a ratio of these capacitances or measurements correlated thereto, which is referred to herein as a duty cycle DCref.

As such, the S1 measurement signal will primarily be affected by application of external pressure to the sensor module and secondarily affected by application of temperature and bending moment. S2 will be primarily affected by changes in temperature applied to the sensor module and secondarily affected by application of pressure and bending moment. S3 will be primarily affected by bending or strain applied to the sensor module and secondarily affected by application of pressure and temperature. In order to measure pressure with a high degree of accuracy, the pressure-sensitive measurement signal S1 having the highest sensitivity to pressure but also affected by temperature and bending moment needs to be compensated for confounding changes in temperature and bending moment. This compensation can be achieved by using the additional measurement signals S2 and S3.

At body temperature of 37 degrees C. and 740 mmHg barometric pressure with no bending applied to sensor module 150, 160, capacitances of the Cref and Cpo capacitors will be substantially equal and can be measured as a 50% duty cycle (calculated as the ratio of Cpo to Cpo+Cref). This duty cycle is referred to herein as DCpo because it is a ratio of a capacitance of Cpo to the sum of capacitances of Cpo and Cref.

Measurement of the capacitance ratios can be provided by charging one capacitance to a reference voltage while discharging the second capacitance to ground. Connecting the two capacitances together to share the charge between them will result in a voltage that is proportional to the ratio of C1 to C1+C2, which is defined herein as a duty cycle, DC. This voltage can then be preconditioned and digitized by a high resolution analog-to-digital converter for digital processing. Reference is made to U.S. Pat. No. 7,623,053 (Terry, et al.) and U.S. Pat. No. 7,714,757 (Denison, et al.), both of which patents are hereby incorporated herein by reference in their entirety. It is recognized that in order to obtain three measurement signals S1, S2 and S3 using three transducer signals 53, 55 and 57 (shown in FIG. 2), signals may be acquired in a time-multiplexed manner.

Measurement of capacitance by providing a voltage proportional to a capacitance ratio is one method for obtaining a signal correlated to changes in capacitance of the transducers due to dynamic physical conditions. Other methods, such as capacitance to time interval conversion and measurement of the time intervals or ratios of the time intervals may be used. Reference is made to U.S. Pat. No. 5,535,752 (Halperin, et al.), hereby incorporated herein by reference in its entirety.

In other embodiments, a duty cycle, or more generally a ratio of signal outputs, can be determined using any time-, voltage-, or other converted measure of the transducer signals shown in FIG. 2. Use of a ratio of the transducer signals in a duty cycle for providing a pressure, temperature, or bend sensitive measurement signal S1, S2 or S3, instead of the transducer signals directly, cancels the influence of any factors that affect the individual transducer signals proportionally or in the same manner, i.e. common mode signals such as certain types of drift. Capacitance measurements and subsequently determined duty cycles of those measurements is one approach to measuring signals S1, S2, and S3, particularly when S1, S2 and S3 are obtained from capacitive transducers. It is recognized that in other embodiments, other signal measurements derived from three transducer signals as shown in FIG. 2 may be substituted in the equations described below for computing a calculated pressure and bending pressure error.

In alternative embodiments, the capacitance-based transducers of the illustrative embodiments presented herein can be substituted for by other types of transducers and measurement signal conversions for measuring the parameters of interest. As an example, strain based measurement of membrane deflection, for example using a piezoresistive film, may be substituted for the capacitive based measurement of pressure-induced membrane deflection used for determining pressure-sensitive signal S1. Similarly, strain-based measurements in a region of the sensor capsule that is substantially sensitive to bend moment, but substantially insensitive to pressure may be substituted for producing S3.

An alternative temperature measurement may be generated by comparison of two circuit parameters that have substantially different temperature responses. For example two circuit reference voltages having two different temperature coefficients may be used to generate a temperature signal S2. It is recognized that numerous sensor module configurations may be conceived for providing transducer signals each having differing sensitivities to pressure, temperature and bending moment and from these transducer signals generating measurement signals S1, S2, and S3, having respective primary sensitivities to pressure, temperature and bending.

Referring again to FIG. 3, hybrid circuit 232 includes an "on-chip" capacitor (Coc) 234 shown schematically in FIG. 3. The on-chip capacitor is insensitive to pressure and bend because it is incorporated in the integrated circuit 232. Coc will be sensitive to temperature-induced changes in charge current. By providing the two air-gap capacitors, Cpo and Cref, an absolute pressure measurement, Pc, can be calculated that is compensated for temperature changes. By adding the third, on-chip capacitor Coc, a pressure bending error, Pb, can be computed. Pb is correlated to pressure changes caused by bending of the sensor module 150, 160. By providing a third capacitor Coc, capacitance measurements, Cpo, Cref and Coc, are available. By acquiring three signals that vary with three unknown influences (i.e. actual pressure changes in the patient's body, temperature-induced pressure changes, and bending-induced pressure changes) a temperature-compensated and bend-compensated pressure signal can be computed.

In the embodiment shown, the combination of Cref and Coc can be considered to be a transducer from which a signal S3 that is sensitive to strain can be determined and can be used in combination with S1 for determining a bending pressure error as will be further described below. In alternative embodiments, another strain-sensitive element could be substituted for determining a signal S3 sensitive to strain in place of the combination of Cref and Coc. For example, a micro-electromechanical system (MEMS) device that is configured as a strain sensor may be included in sensor module 150, 160. A MEMS device may be positioned along the sensor housing 270, 280, off of a neutral axis of the sensor housing 270, 280, such that it is subjected to bending moments applied to sensor module 150, 160 and produces a signal that is correlated to the applied bending moment. In other embodiments, other types of strain sensors may be used to provide the signal S3 having a primary sensitivity to strain.

Figure 4:
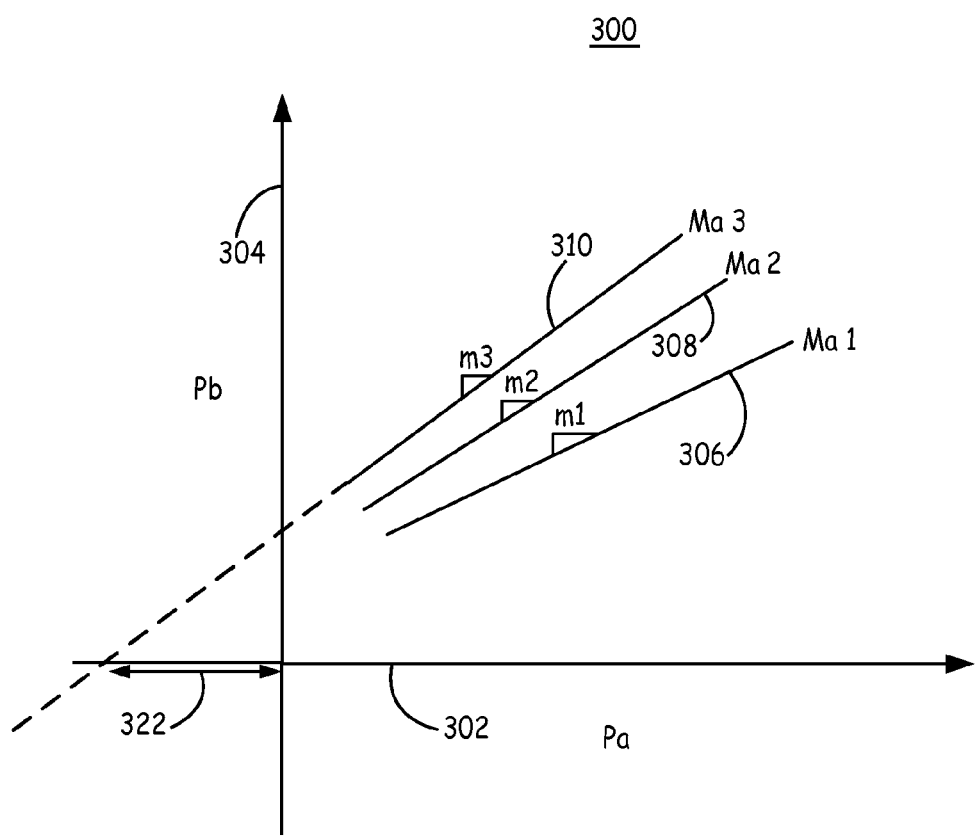
FIG. 4 is a first order plot of bending pressure error as a function of actual applied pressure (under varying applied bending moments).

FIG. 4 is a first order plot 300 of pressure bending error Pb 304 as a function of actual applied pressure (Pa) 302 under varying applied bending moments, Ma1, Ma2 and Ma3. As applied pressure increases, the influence of bending on the pressure sensor causes an increase in the measured pressure. This bending-induced pressure increase, Pb 304, increases in a substantially linear manner with increasing applied pressure over expected operation conditions as shown by plotted lines 306, 308 and 310. The slope of this linear relationship, however, changes with different applied bending moments, Ma1, Ma2, and Ma3 as shown by lines 306, 308, and 310 having distinct slopes m1, m2, and m3, respectfully. A second order influence of Pa on Pb is included in the following equations, but not represented in FIG. 4 for the sake of simplicity of the illustration.

In order to determine an exact value for Pb, both the actual bending moment, Ma, applied to the sensor and the actual applied pressure, Pa, would need to be known. Since the actual bending moment and actual applied pressure are unknown under implant conditions, estimates correlated to Ma and Pa are used along with calibration constants to compute an estimate of Pb.

In one embodiment, a general equation for pressure bending error Pb is given by:

$$Pb = f(DCpo, ADCtemp) \times mf \quad [1]$$

wherein f(DCpo, ADCtemp) is a function of DCpo (representing S1 described above) and ADCtemp (representing S2). ADCtemp is a digitally-converted independent measurement of temperature that is based on comparison of two circuit parameters having different temperature responses. The term mf represents a moment fraction, which will be described in further detail below.

DCpo is defined above as the duty cycle of the air-gap, pressure-sensitive capacitor Cpo and the air-gap capacitance Cref and is given by a ratio of the capacitances Cpo to Cpo+Cref. DCpo will be highly sensitive to changes in applied pressure and thus a function of DCpo can be used to account for the influence of applied pressure Pa on Pb, as shown by the relationship plotted in FIG. 4. A calculated pressure Pc, which is compensated for temperature but not bending, is a function of DCpo. Accordingly, the term f(DCpo, ADCtemp) could be replaced by a function of the calculated, temperature-compensated pressure Pc, f(Pc), in some embodiments.

The moment fraction term mf in Equation 1 is a fractional measure of the bending applied to the pressure sensor. The mf is the ratio of actual bending applied to the sensor and the maximum bending expected under operating conditions. The mf can vary between 0 (no bending applied) and 1 (applied bending equals maximum bending expected under operating conditions). Since an actual applied moment Ma is not measured by the pressure sensor, a relative change in bending moment determined as a fraction of the maximum bending can be used to estimate the effect of applied bending on the slope of the Pb vs. Pa relationship. The moment fraction is computed using capacitance measurements obtained from the three sensor capacitors, Cpo, Cref, and Coc, as will be further described below.

In Equation 1, the f(DCpo, ADCtemp) may be expressed as a linear function. For example, when determined as a function of Pc:

$$f(DCpo, ADCtemp) = F \times (Pc - G) \quad [2]$$

wherein G is the intercept 322 shown in FIG. 4 and F is the slope of Pa vs. Pb under a constant bending moment. When Equation 2 is substituted into Equation 1, Pb becomes:

$$Pb = F \times (Pc - G) \times mf \quad [3]$$

In a first order estimation, the term mf can be thought of as a "slope adjustment" term because the term mf×F defines the first order slope of the Pb vs. Pa relationship, which is mf dependent. During a calibration procedure, the pressure bending error Pb of a calculated temperature-compensated pressure measurement Pc can be measured relative to an actual applied pressure. The slope F and intercept G can then be determined during a calibration procedure when a known moment fraction is applied and at least two different actual pressures are applied. A calibration procedure for determining F and G in Equation 3 will be further described below.

In one embodiment, moment fraction, mf, is computed by:

$$mf = H(DCref - DCref^0) + K(Pc - Pc^0) + L(ADCtemp - ADCtemp^0) \quad [4]$$

wherein H, K and L are constants. Equation 4 could be considered generally as $mf = H^*(S3-c3) + K(S1-c1) + L^*(S2-c2)$ where H, K and L are calibration coefficients and $c1$, $c2$ and $c3$ correspond to constants determined as the measurement signals S1, S2, and S3 measured at zero bending moment and at a controlled pressure and temperature.

In Equation 4, S3 is represented as DCref, the ratio of the capacitances Cref to Cref+Coc. $DCref^0$ is DCref measured at zero bending moment for a controlled temperature and applied pressure. S1 is represented as the calculated, temperature-compensated pressure Pc, and $Pc^0$ is Pc measured at zero bending moment for a controlled temperature and applied pressure. S2 is represented as ADCtemp, a digitally-converted temperature measurement, and $ADCtemp^0$ is the temperature measurement at a controlled temperature and pressure when zero bending moment is applied.

Cref and Coc capacitance measurements will be affected substantially equally by measurement circuit changes. Coc will not be sensitive to bending because it is integrated in the hybrid circuit board. DCref will therefore be influenced by bending as Cref changes due to bending but is normalized by changes in measurement circuit variation (and therefore is largely insensitive to temperature change). The relative difference between DCref and $DCref^0$ when pressure and temperature are held constant but bending moment changes from zero to some unknown amount of bending will therefore be correlated to the relative change in bending moment. This relative change can be used in estimating a moment fraction mf.

In alternative embodiments, another electrical signal correlated to a relative change in bending moment may be substituted for the $(DCref - DCref^0)$ term in Equation 4. For example, if a strain sensor embodied as a MEMS device is incorporated in the sensor module housing as described in conjunction with FIG. 3, the MEMS device signal may be used to determine a relative change in bending moment that is substituted for $DCref - DCref^0$.

In addition to bending induced changes of Cref, DCref will be affected by pressure changes that may alter Cref. The relative change between DCref and $DCref^0$ will therefore depend on both bending moment and pressure changes. A second term, $(Pc - Pc^0)$, is therefore included in the mf Equation 4 to account for the effect of pressure-related influences on Cref and DCref. Pc and $Pc^0$ are pressure measurements that have been compensated for temperature changes. The relative change in Pc from $Pc^0$ at a fixed temperature and applied pressure will be related to changes in the applied bending moment and are thus also included in the mf Equation 4.

A third term, "$L(ADCtemp - ADCtemp^0)$" is included in Equation 4 to account for higher order influences of temperature on DCref and Pc. In some embodiments, the constant L may be assumed equal to 0, eliminating the third term from Equation 4. If temperature sensitivity of Pb is found to exist for a specific sensor module design, the constants L and $ADCtemp^0$ can be determined using the calibration procedure described below, repeated for at least two temperatures.

The terms $DCref - DCref^0$ and $Pc - Pcref^0$, multiplied by respective coefficients H and K included in Equation 4, provide a measure related to the changes in the capacitor measurements of Cpo and Cref, provided as duty cycles, due to relative changes in bending moment. The constants $DCref^0$, $Pc^0$, H and K (and optionally L) in Equation 4 are determined in a calibration procedure as further described below. This relative change in bending moment is computed as a moment fraction, i.e. a relative change of duty cycles measured during an applied bend from duty cycles measured at a zero bending moment. The moment fraction is used in Equation 3 to reflect the influence of bending moment on the slope of the Pb vs. Pa relationship.

More specifically, the moment fraction computed using capacitances Cpo, Cref, and Coc is used to "correct" the slope of the equation F(Pc−G) defining the relationship of Pb and Pa because the first order slope of this relationship is dependent on applied moment as shown in FIG. 4. Note that when Equation 4 is substituted into Equation 3, the expanded form includes a second order term ($Pc^2$) that is not represented in the illustrative plots shown in FIG. 4. The second order term $Pc^2$ will cause the plots shown in FIG. 4 to be non-linear, for example a parabolic function of Pa instead of the linear dependence of Pb on Pa as shown.

Figure 5A:
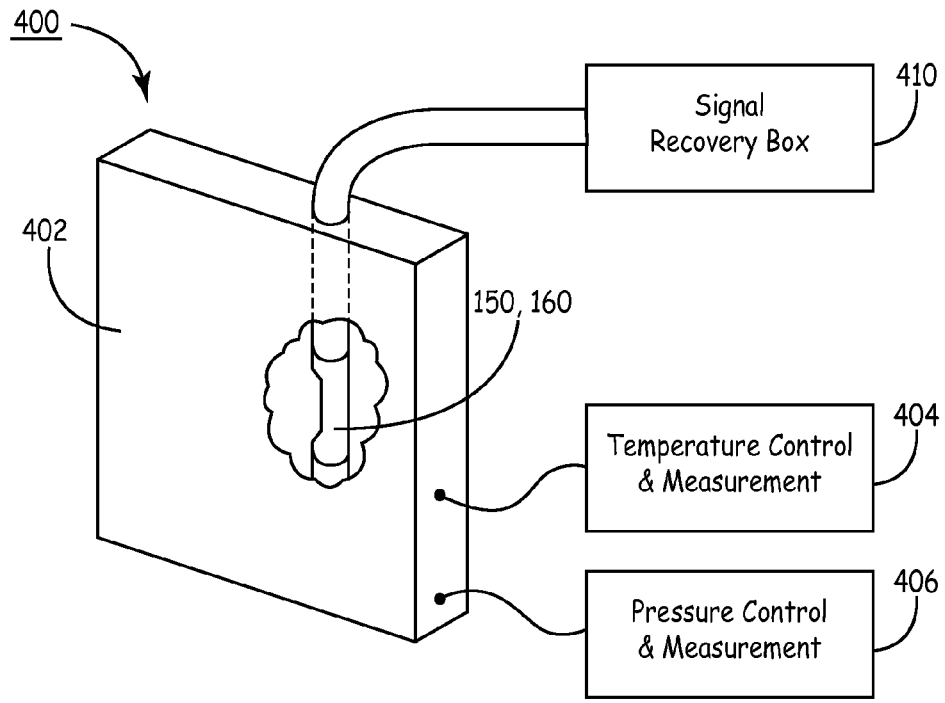
FIGS. 5A and 5B show calibration test fixture apparatus used during a calibration procedure for establishing equation coefficients for computing a bending pressure error.
Figure 5B:
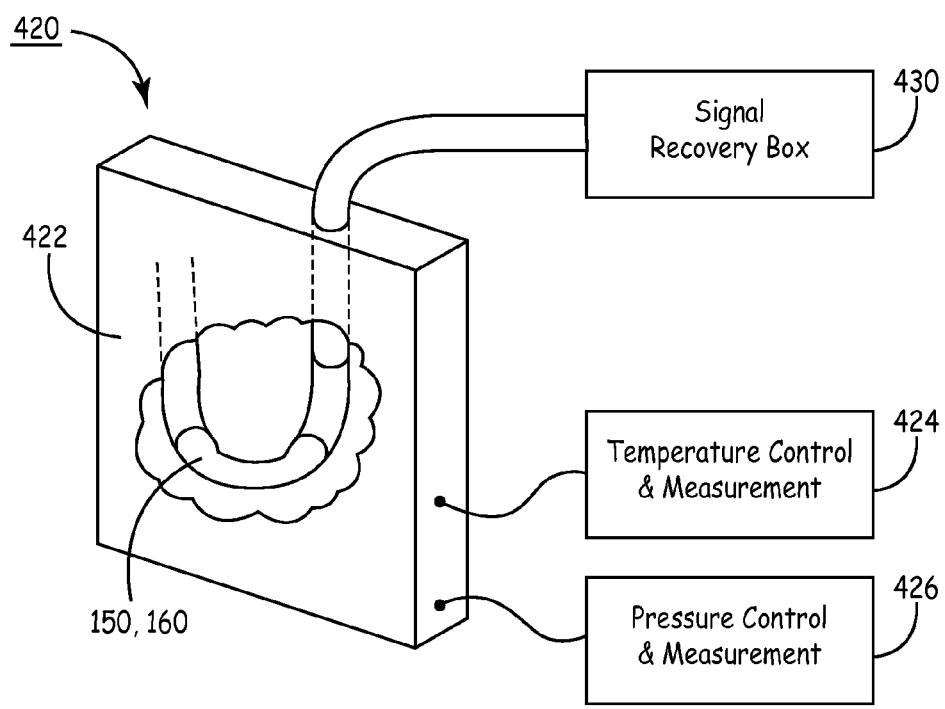

FIGS. 5A and 5B show calibration test fixture apparatus 400 and 420 used during a calibration procedure for determining values needed for computing Pb. In FIG. 5A, test fixture apparatus 400 includes a test fixture 402 to completely enclose sensor module 150, 160 and to hold module 150, 160 in a zero bending moment position. A temperature control and measurement module 404 applies a controlled temperature inside test fixture 402 and measures the actual applied temperature. A pressure control and measurement module 406 applies a controlled amount of pressure inside fixture 402 and measures the actual applied pressure.

A signal recovery box 410 receives signals from sensor module 150, 160 during a calibration procedure. Capacitances, capacitor charge time intervals, duty cycles, converted analog voltage signals, and/or digitally converted signals needed to compute Pc and determine Pb are recorded.

In FIG. 5B, test fixture apparatus 420 includes a test fixture 422 to completely enclose sensor module 150, 160. Test fixture 422 is designed to hold sensor module 150, 160 in a maximum bending moment configuration corresponding to a maximum strain expected during sensor operating conditions. This maximum moment position may be based on in vivo images of a sensor module deployed to a selected site for monitoring pressure. By holding the sensor module 150, 160 in a zero bending moment position (in fixture 402) and a maximum bending moment position (in fixture 422) calibration constants needed for computing Pb can be determined without actually measuring bending moment. This test fixture apparatus thereby eliminates the need to apply and measure controlled amounts of bending moment.

A temperature control and measurement module 424 applies a controlled temperature inside test fixture 422 and measures the actual applied temperature. A pressure control and measurement module 426 applies a controlled amount of pressure inside 422 and measures the actual applied pressure.

A signal recovery box 430 receives signals from sensor module 150, 160 during a calibration procedure. Capacitances, capacitor charge time intervals, duty cycles, converted analog voltage signals, and/or digitally converted signals needed to compute Pc and Pb can be recorded or transferred to a microprocessor for processing and determination of calibration constants.

While test fixture apparatus 400 and 420 are shown as separate systems in FIGS. 4A and 4B, it is recognized that the test apparatus may be a single system configurable with two different test fixtures 402 and 422. Alternatively a single test fixture 402, 422 may be provided that allows the bending moment applied to the sensor module 150, 160 to be adjusted between at least a zero bend position and a maximum bending position with intermediate bending positions optional.

Figure 6:
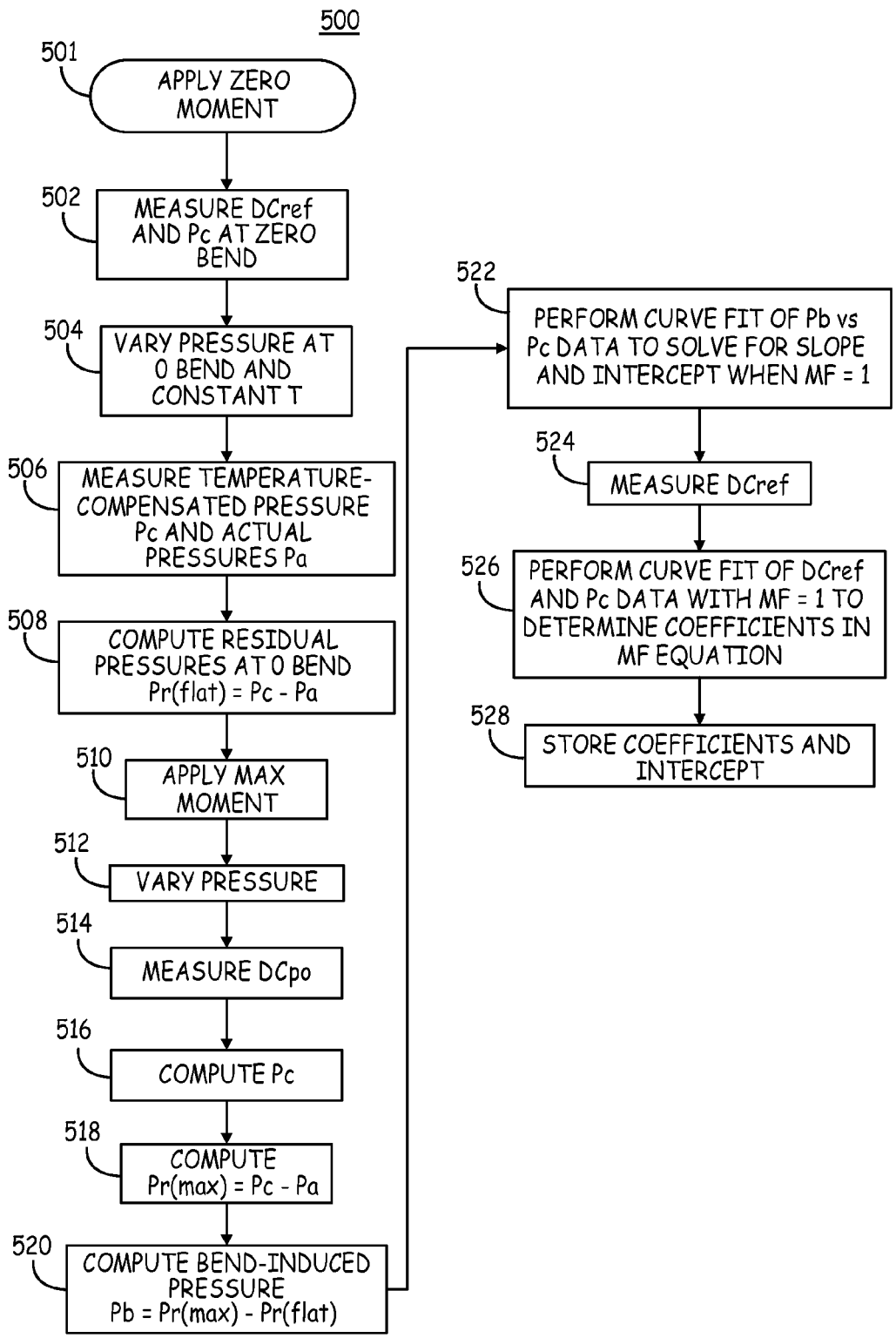
FIG. 6 is a flow chart of one method for establishing equation coefficients for computing a bending pressure error.

FIG. 6 is a flow chart 500 of one method for establishing equation coefficients for computing a pressure bending error for use in correcting a calculated pressure measurement during pressure monitoring. Flow chart 500 and other flow charts presented herein are intended to illustrate the functional operation of a medical device system, and should not be construed as reflective of a specific form of software or hardware necessary to practice the methods described. It is believed that the particular form of software will be determined primarily by the particular system architecture employed in the device for signal sensing and monitoring. Providing software to accomplish the described functionality in the context of any modern IMD system, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software. A computer-readable medium may further include non-volatile media such as flash memory or EEPROM that is contained within the sensor module that can be accessed by a communications method, such as that represented in the above-incorporated '178 patent (Reinke, et al).

The process shown by flow chart 500 is typically performed prior to implantation or deployment of the sensor. For example, the process is performed using the test apparatus shown in FIGS. 4A and 4B which allow controlled temperature, controlled pressure and controlled bend to be applied. Controlled bend is achieved by holding the sensor in a neutral position (zero bend) and by imposing a shape on the sensor using a specialized fixture in test apparatus 420. The imposed shape corresponds to a maximum bending moment expected to occur during operating conditions.

At block 501, zero bending moment is applied to the sensor module, and $Pc^0$ and $DCref^0$ are measured at block 502. These zero-bending reference measurements are stored as constants and used for computing the moment fraction as given by Equation 4. $Pc^0$ and $DCref^0$ are recorded at a single controlled value of pressure and temperature. For example, $Pc^0$ and $DCref^0$ may be recorded at zero bending moment, 37 degrees C., and 740 mmHg.

At block 504, the pressure is varied between controlled settings. Zero bending moment and a constant temperature, e.g. 37 degrees C., are applied. The actual applied pressure is recorded and the temperature-compensated pressure Pc is calculated for a selected number of applied pressures at block 506. The actual applied pressure may be varied over a range of expected operating pressures. For example the pressure may be varied between approximately 450 mmHg and 900 mmHg.

At block 508, the error of Pc relative to the actual applied pressure Pa is determined as the difference between the two. The error can be referred to as the residual pressure at 0 bending ($Pr_{flat}$). This difference between an actual pressure and computed pressure at zero bending can be considered an offset. Knowing $Pr_{flat}$ over a range of actual applied pressures, Pa, and calculated pressures Pc, allows calibration coefficients to be solved for in the moment fraction equation as further described below.

At block 510, a maximum moment is imposed on the sensor module. The actual bending moment or strain applied is not necessarily measured in a quantitative value. Rather, a shape is imposed on the sensor module that corresponds to a maximum strain or bending of the module expected during sensor operation after deployment. In this position, the sensor module is considered to have a moment fraction of 1. As such the moment fraction term in Equation 3 can be set equal to one when solving for coefficient F and intercept G. Similarly, moment fraction on the left side of Equation 4 can be set equal when solving for coefficients H and K.

In order to solve for the coefficient F and intercept G in Equation 3, measurements of Pb and Pc are needed at two or more applied pressures when mf is 1. At block 514, DCpo (or an analog or digital converted measure thereof) is measured for at least two different applied pressures. For example, pressure may be varied in equal steps over a range of approximately 450 mmHg to approximately 900 mmHg.

Using DCpo, or an analog voltage or digitized signal correlated thereto, Pc is computed at block 516 for each applied pressure. A residual pressure error at the maximum bending moment ($Pr_{max}$) is computed as the difference between Pc and the actual applied pressure Pa at block 518.

Error caused by bending, Pb, in the calculated pressure Pc, is the difference between the residual pressure measured at maximum moment $Pr_{max}$ and the residual pressure or offset measured at zero bending ($Pr_{flat}$) for a given applied pressure. This bending-induced pressure change Pb is computed at block 520 for each applied pressure.

In Equation 3, moment fraction is set to 1 (maximum moment fraction) leaving Pb=F(Pc−G). Having computed the values of Pb over a range of pressures and knowing the corresponding calculated Pc at the same applied pressure allows a curve of Pb vs. Pc to be generated. A curve fitting method is applied to the Pb and Pc data to solve or the slope F and intercept G of Equation 3 at block 522. In an alternative embodiment, Equation 3 may be written as Pb=F(DCpo−G) and a curve of Pb and DCpo data is generated and F and G are solved for.

In order to solve for the coefficient H and K in Equation 5, DCref and Pc data are needed over a range of applied pressures, which could be as few as two applied pressures. When moment fraction is set equal to 1 (maximum bending), and $DCref^0$ and $Pc^0$ are known values previously measured at block 502, H and K are two unknowns that can be solved for using DCref and Pc measurements at varying applied pressure.

Accordingly, DCref is measured at block 524 at maximum bending moment for at least two of the same actual pressures applied when Pc was computed at block 516. It is recognized that DCref may be measured at the same time Pc was computed at block 516. It is further noted that the order of the blocks shown in flow charts presented herein may be changed and in some cases some steps may be omitted or other steps may be added and the final result of obtaining an equation to establish Pb using capacitance measurements for correcting a calculated pressure measurement can still be achieved successfully.

At block 526, the coefficients H and K are solved for by applying curve-fitting techniques to the DCref vs. Pc data when mf is set equal to 1. At block 528, $DCref^0$, $Pc^0$, coefficients F, H and K and the intercept G are stored as constants in memory of an IMD (or other processing device) for use in calculating a bending-induced pressure Pb during sensor operation (or later offline) using Equations 3 and 4.

Figure 7:
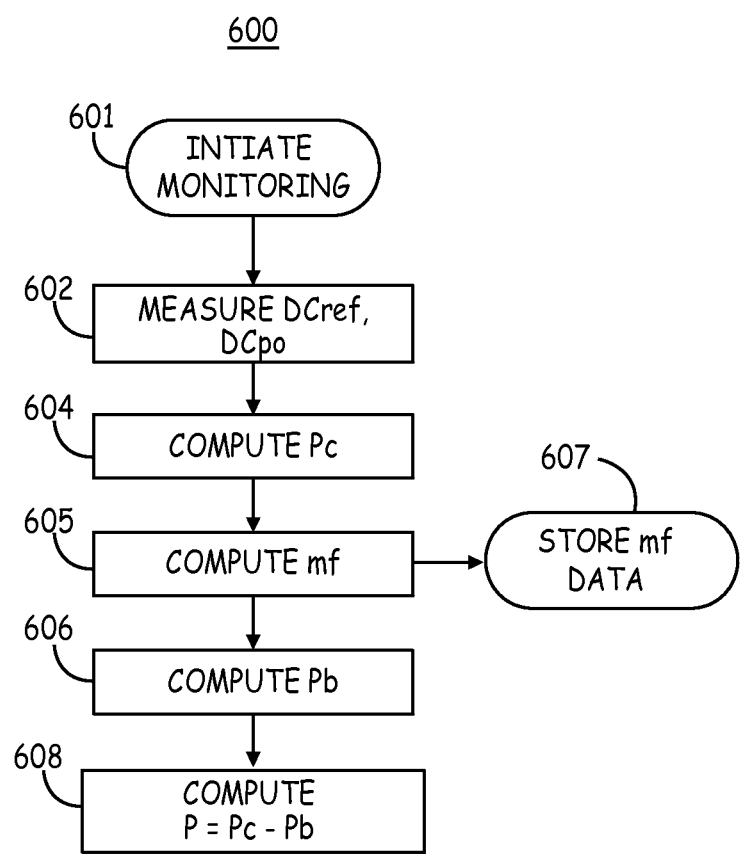
FIG. 7 is a flow chart of a method for monitoring a pressure signal according to at least one embodiment.

FIG. 7 is a flow chart 600 of a method for monitoring a pressure signal according to one embodiment. At block 601, pressure monitoring is initiated according to a programmed monitoring protocol. In various embodiments, pressure monitoring may be performed continuously, at programmed intervals, or on a triggered basis in response to detecting an event using another physiological signal or initiating, stopping, or adjusting a delivered therapy.

At block 602, capacitances of Cref, Cpo, and Coc are measured to compute duty cycles DCref and DCpo. As described previously, DCref is a ratio of the air gap reference capacitor Cref and the sum of Cref and Coc. DCpo is a ratio of Cpo and the sum of Cpo and Cref. As will be described further below, a third duty cycle may be computed using a ratio Cpo and the Coc to use in place of DCpo in Equation 1 above.

At block 604, Pc is calculated using DCpo, which may be first converted to a digital signal with a gain and offset applied. Pc may be determined as generally described in the above-incorporated Halperin '752 patent. In general, Pc represents a pressure measurement which is compensated for temperature changes but is not corrected for error due to bending of the sensor module. In other embodiments, Pc may be a calculated pressure measurement that does not include temperature compensation. Pc may be computed according to any implemented method for measuring pressure using a pressure sensor module.

At block 605, the moment fraction, mf, is computed using Equation 4 and the stored constants, $DCref^0$, $Pc^0$, coefficients H and K determined in the method shown in FIG. 6 (and optionally L and $ADCtemp^0$. The measured signals DCref and Pc obtained at blocks 602 and 604 are provided as input for computing mf.

The mf may be stored at block 607 for use in monitoring strain applied to the sensor module. Having a record of mf data can provide valuable design information or sensor operating conditions. If a high mf is repeatedly measured, a clinician may want to reposition the sensor module to a location where it is exposed to less strain. For example, if a mf greater than 1 is measured, the sensor module is experiencing greater strain than a maximum anticipated mf. This or another threshold may be used for triggering a warning that the sensor should be repositioned, replaced, or may produce results including significant error, as further described below in conjunction with FIG. 9.

A record of the mf data stored at block 607 can be useful in determining sensor module design specifications and lead specifications. When an actual bending moment Ma applied during calibration is known, the product of Ma and a measured mf (Ma×mf) may be determined and stored at block 607 to provide estimates of actual bending moments applied to the sensor.

At block 606, bending pressure error Pb is computed. Pb is computed using Equation 3 above, the calculated mf, stored coefficient F and intercept G determined during the process shown in FIG. 6, and the measured DCpo or Pc provided as input.

In some embodiments f(DCpo, ADCtemp) as shown in Equation 1, may use an alternative duty cycle that is measured using capacitance measured from the on chip reference capacitor Coc. For example, a duty cycle DCpo used in Equation 1 in the term f(DCpo, ADCtemp) may be a ratio of Cpo and the sum of capacitances Cpo and Coc instead of Cref. Similar to Cref, Coc will vary with influences of temperature on charging current. Coc will be insensitive to pressure and bending changes and can therefore be used as a reference signal for normalizing Cpo to correct for temperature-induced changes in charging current (but will not correct for temperature-induced changes in capacitance due to changes in pressure inside the sensor module).

At block 608, a corrected pressure measurement P is computed, which is corrected or compensated for bending-induced changes in Cpo and Cref. The bend-compensated pressure P is the difference between Pc and Pb. This corrected pressure measurement may then be used for monitoring a patient condition, detecting a physiological condition, monitoring the effectiveness of a therapy or the need to adjust a therapy, or the like. Any medical pressure monitoring application may implement the bend compensation apparatus methods described herein to correct pressure measurements for the effects of strain on the pressure sensor module when the module is subjected to bending forces. Furthermore, any pressure monitoring application may utilize the apparatus and methods described for correcting a pressure measurement for bending-induced changes in a measured pressure signal that are based on capacitive changes of a capacitor.

Figure 8:
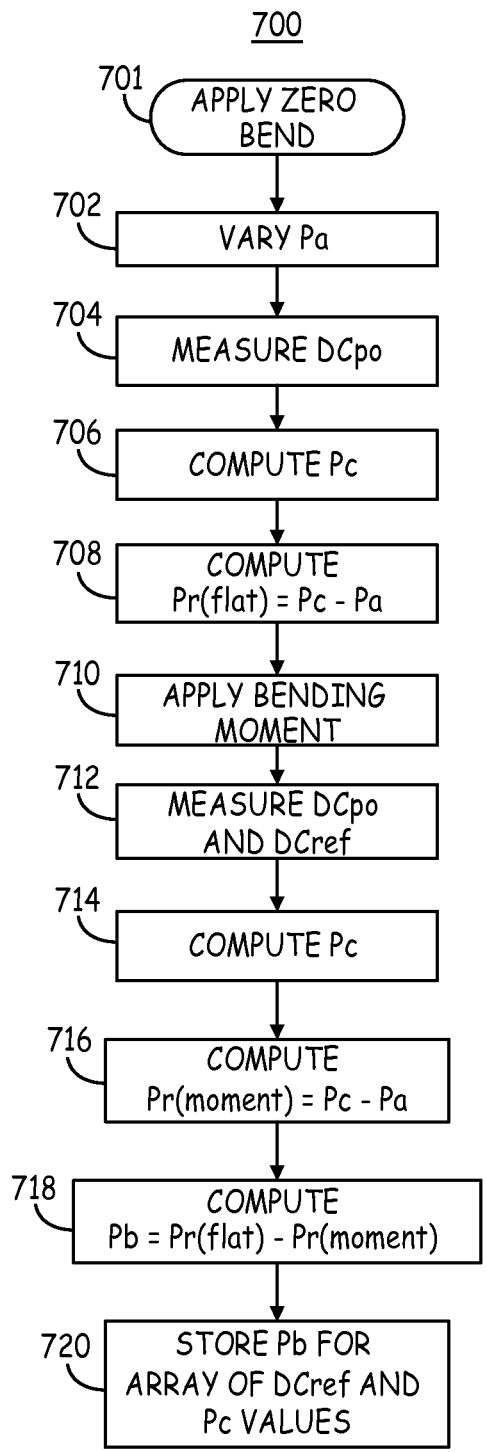
FIG. 8 is a flow chart of an alternative embodiment for establishing values of pressure bending error Pb.

FIG. 8 is a flow chart 700 of an alternative embodiment for establishing values of bending pressure error Pb. Instead of generating and storing constants used in an equation for computing Pb using measured values of DCref and Pc, a look-up table of Pb values can be generated prior to deploying the sensor module. The look-up table of Pb values is then stored in an IMD (or in association with an external processor receiving data from the IMD) and used for correcting a calculated pressure measurement for bending error.

At block 701, zero bending is applied to the sensor module using test apparatus 400. The applied pressure is varied at block 702 over a range of expected operating pressures. The temperature is controlled at a constant value, for example, 37 degrees C.

At block 704, DCpo is measured and the calculated pressure Pc is computed using DCpo at block 706. At block 708, the residual pressure Pr(flat) is computed as the difference between the calculated pressure Pc and the actual applied pressure Pa.

After obtaining Pr(flat) for a range of applied pressures at zero bending moment, a non-zero bending moment is applied to the sensor module at block 710. Bending moment may be varied over a range of bending moments by applying varying degrees of bending to the sensor module using test fixture 402, 422. Alternatively, a maximum bending moment may be applied. Pb is measured over a range of actual pressures at the maximum bending moment. Pb values between the applied zero bending and maximum bending for the range of applied pressures may then be interpolated. The resolution of Pb values will depend on the number of bending moments and pressures applied. A minimum of two pressures, for example a minimum and maximum expected operating pressure, and two bending moments, for example zero and maximum bending, are applied to obtain Pb values. Additional Pb values may then be interpolated or extrapolated from the measured Pb values.

At block 712, DCpo and DCref are measured. Pc is computed using the DCpo measurement at block 714. The residual pressure at the applied bending moment, Pr(moment), is computed as the difference between the calculated pressure Pc and the applied pressure Pa at block 716. The bending pressure error Pb is computed as the difference between Pr(flat) and Pr(moment) for a given applied pressure Pa.

Pb is stored in a look-up table of values for an array of measured DCref and calculated pressure Pc values at block 720. During sensor operation, the measured DCref and calculated Pc are used to look-up a value of Pb from the look-up table. Pb can then be subtracted from Pc to compute a corrected pressure measurement P. In an alternative embodiment, a look up table of values of Pb may be generated for an array of DCref and DCpo values.

Figure 9:
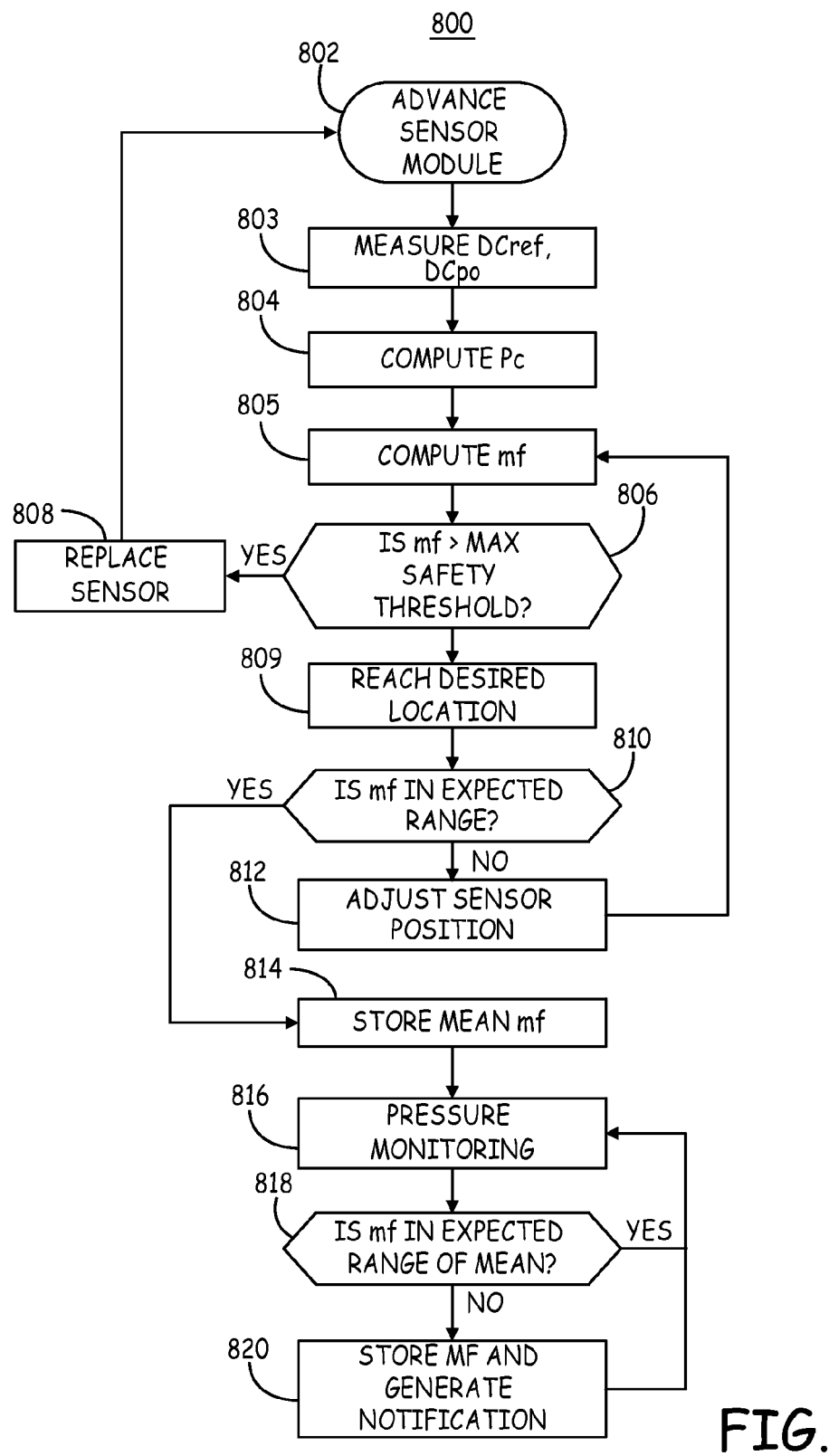
FIG. 9 is a flow chart of a method for using a sensor module.

FIG. 9 is a flow chart 800 of a method for using a sensor module. In some embodiments, a method for using a sensor module does not include performing all of the functions described in conjunction with blocks 802 through 820.

At block 802 a sensor module is advanced along a pathway to a desired implant location where the sensor will be positioned for monitoring pressure. Oftentimes, a sensor is delivered through a catheter which may follow an intra- or extravascular, torturous pathway. The handling and delivery of the sensor during an implant procedure could result in severe bending of the sensor housing while it is advanced to an implant site.

At locations along the way to a desired implant site, DCref and DCpo are measured at block 803 to allow computation of Pc at block 804. During this process, the lead may be temporarily connected to an IMD or to an external device configured to compute mf during the implantation procedure. In alternative embodiments, a strain sensor is used to monitor mf without the computation of Pc.

The mf is then computed at block 805 and compared to a maximum safety threshold at block 806. The maximum safety threshold is a value of mf that is selected to correspond to bending of the sensor housing beyond acceptable limits. For example, a safety threshold may be a mf of approximately 2 in one embodiment, i.e., twice the expected maximum mf during operation. Such a high mf may result in damage to the sensor. An audible or visual warning that sensor strain has exceeded acceptable limits or may be damaged and should be replaced may be automatically generated at block 808. The sensor is replaced by a new sensor is advanced by returning to block 802.

When it is believed that the sensor module has reached a desired location, the mf is compared to an expected range at block 810. For example, if the mf is greater than 1, then the clinician will know that the sensor module is under greater strain than expected and outside an operating calibration range. The sensor module may be positioned in a high flow or high motion region that is not a targeted monitoring location or the lead may be improperly positioned causing unexpected strain on the sensor module. A clinician may adjust the lead position or advance the sensor to a different location at block 812 until the mf is within an expected operating range.

In some embodiments, the targeted location may be a location associated with some bending of the lead due to physiological motion of anatomical structures, such as cardiac motion, or due to blood flow, such as in the right ventricular outflow tract. In such embodiments, the expected mf may be above some minimum value but not more than 1. During implantation, a mf less than an expected range may indicate that the sensor module is not yet in a desired location and a mf greater than a clinically identified threshold value but not more than 1 may indicate that the sensor module is positioned in a targeted location.

Once the sensor module is determined to be operating within an expected range of the mf at block 810, a mean mf value is determined and stored at block 814. The mean mf may be computed from sampled mf measurements obtained over an interval of time. This mean mf provides a baseline mf value that may be used for later comparisons to mf measurements to determine if the positioning of the lead and sensor change over time, which may influence pressure recordings.

At block 816, normal sensor operation is initiated and pressure monitoring is performed according to an implemented monitoring protocol. Whenever a strain-compensated pressure is computed, the mf used in correcting the pressure measurement for strain-induced error can be compared to an expected operating range, which may be defined as a range around the mean mf stored at block 814. If the mf is within the expected operating range, pressure monitoring continues according to a programmed algorithm by returning to block 816.

If the mf is outside the expected range, the mf measurement is stored and a notification is generated at block 820. An out-of-range mf notification may take various forms. In one embodiment, the notification is a flag of the pressure measurement(s) taken using the out of range mf measurement. A flag or notation of such pressure measurements indicates that the pressure measurement(s) have been probably been obtained outside the calibrated operating range of the sensor and therefore may not be represent reliable data.

The notification may additionally or alternatively include a patient or clinician alert that is produced by the IMD or transmitted from the IMD to an external device to alert the patient or clinician to a change in the sensor module operating conditions. The out-of-range mf measurement may indicate sensor module or lead dislodgment or displacement or other issues which may require replacement or repositioning of the sensor module.

The notification generated at block 820 may additionally or alternatively include a mf data report. The report may be stored by the IMD and produced as mf data is accumulated until an interrogation request. In response to an interrogation request from an external device, the mf data report is transmitted by IMD communication circuitry to an external device for review by a user. The report will typically include the date and time of out-of-range mf measurements and may additionally include in-range mf measurements. Such a report can provide clinical researchers and engineers valuable information in interpreting and understanding pressure data acquired by the sensor module and the operating conditions of implanted leads and sensor modules. This information can be used to optimize lead and sensor module mechanical design or adjust calibration ranges of the sensor module prior to implanted, e.g. the maximum bending moment applied to the sensor module during calibration as described above.

In alternative embodiments, a comparison to an established normal operating range is not required. Moment fraction measurements that are made in conjunction with every pressure measurement (or made less or more often) can be accumulated in a report that is uplinked to an external device. The report of accumulated mf data can be used in pressure data interpretation and/or in sensor module design and calibration. In some embodiments, mf measurements may be obtained at times other than times that a pressure measurement is obtained or required.

Moment fraction measurements may be determined according to a monitoring algorithm that is independent of a pressure monitoring algorithm. A transducer or combination of transducers sensitive to strain may be used to measure and report a moment fraction (or estimated bending moment using the product of mf and a calibration applied bending moment). Moment fraction measurement may be used for the purposes of monitoring for lead or sensor module displacement, dislodgment or other issues and/or to collect data for design and calibration purposes. A notification that the lead or sensor may be damaged due to excessive bending moments beyond an established safety limit, e.g. 2, or should be replaced due to mf beyond an anticipated maximum operational mf, e.g., 1, may be generated, even when mf is not used to correct a pressure measurement (or other measurement performed by the sensor module).

In some embodiments, a bend-corrected pressure measurement may not be computed using mf at all. Instead, the mf and/or an indication that mf may be causing insignificant, moderate or significant error due to low, moderate or high mf measurements may be reported at block 820. If mf becomes high, for example 0.75 or higher, other procedures, such as Swan-Ganz catheterization may be recommended for verifying pressure measurements.

In other embodiments, bend-corrected pressure measurements may be recommended or computed for only some ranges of mf, where it is determined that the mf would cause significant error. For example if mf is less than 0.25, no bend correction may be performed; any error may be small or negligible. If mf is between 0.25 and 0.75, bend correction may be clinically relevant and this knowledge can be taken into account when interpreting pressure measurements. Pb may be reported along with Pc and bend correction may be optional. If mf is greater than 0.75, bending error is considered significant and bending correction recommended, done automatically, or both corrected and non-corrected pressure measurements reported.

Pulsatile variability in mf may be monitored or detected to discriminate between pulsatile changes in mf and a static offset. The proportion of pulsatile variability and static offset of the mf may be reported in a notification at block 820, for use by a clinician in interpreting pressure measurements or by an engineer for design purposes.

Thus, apparatus and associated methods for providing measurements of moment fraction of a sensor module have been presented in the foregoing description with reference to specific embodiments. It is appreciated that various modifications to the referenced embodiments may be made without departing from the scope of the disclosure as set forth in the following claims.

The invention claimed is:
1. A sensing system for providing signals representative of a magnitude of moment fraction applied to an implantable sensor at a selected site, comprising:
   a sensor module comprising
      a first transducer producing a first signal having an associated first response to pressure and bending applied to the sensor module, and
      a second transducer producing a second signal having an associated second response to pressure and bending applied to the sensor module, the second response different than the first response; and
   a processor programmed with instructions to cause the processor to compute a moment fraction in response to the first signal and the second signal and generate a notification in response to the moment fraction.

2. The system of claim 1, wherein at least one of the first transducer and the second transducer is a capacitive transducer.

3. The system of claim 1, wherein the second transducer comprises a microelectromechanical system (MEMS) device.

4. The system of claim 1, wherein the processor is configured to compute a calculated pressure using the first signal, the calculated pressure comprising an error due to bending of the sensor module, and to compute the moment fraction using the calculated pressure and the second signal.

5. The system of claim 1, wherein the second transducer comprises:
   a first component and a second component, the first component producing a first output having a first response to bending and temperature applied to the module and the second component producing a second output having a second response to bending and temperature applied to the module, the second component output response being different than the first component output response;
   the processor configured to compute the second signal using the first output and the second output.

6. The system of claim 5, wherein the processor is configured to compute a calculated pressure from the first signal and one of the first component output signal and the second component output signal, and compute the moment fraction using the calculated pressure and the second signal.

7. The system of claim 1, wherein the notification comprises a report of accumulated moment fraction data.

8. The system of claim 1, wherein the processor is further configured to establish a normal operating range of the moment fraction and compare the computed moment fraction to the operating range, the notification generated in response to the computed moment fraction being outside the normal operating range.

9. The system of claim 8, wherein the notification comprises an alert to reposition the sensor module.

10. The system of claim 8, wherein the processor is further configured to compute a bend-compensated pressure using the computed moment fraction,
   the notification comprising a data flag of the bend-compensated pressure computed using a moment fraction that is outside the established normal operating range.

11. A method for providing signals representative of a magnitude of moment fraction applied to a sensor at a selected site, the method comprising:
   measuring a first signal produced by a first transducer, the first signal having an associated first response to pressure and bending applied to a sensor module comprising the first transducer and a second transducer,
   measuring a second signal produced by the second transducer, the second signal having an associated second response to pressure and bending applied to the sensor module;
   computing a moment fraction in response to the first signal and the second signal; and generating a notification in response to the moment fraction.

12. The method of claim 11, wherein measuring at least one of the first signal and the second signal comprises measuring a capacitive transducer signal.

13. The method of claim 11, wherein measuring the second signal comprises measuring a microelectromechanical system (MEMS) device signal.

14. The method of claim 11, further comprising computing a calculated pressure using the first signal, the calculated pressure comprising an error due to bending of the sensor module, and computing the moment fraction using the calculated pressure and the second signal.

15. The method of claim 11, wherein the second transducer comprises:
measuring a first output of a first component of the second transducer;
measuring a second output of a second component of the second transducer; the first output having a first response to bending and temperature applied to the sensor module and the second output having a second response to bending and temperature applied to the module, the second output being different than the first output;
computing the second signal using the measured first output and second output.

16. The method of claim 15, further comprising computing a calculated pressure from the first signal and one of the first output and the second output; and
computing the moment fraction using the calculated pressure and the second signal.

17. The method of claim 11, wherein generating the notification comprises generating a report of accumulated moment fraction data.

18. The method of claim 11, further comprising establishing a normal operating range of the moment fraction;
comparing the computed moment fraction to the normal operating range; and
generating the notification in response to the computed moment fraction being outside the normal operating range.

19. The method of claim 18, wherein generating the notification comprises generating an alert to reposition the sensor module.

20. The method of claim 18, further comprising computing a bend-compensated pressure using the computed moment fraction,
wherein generating the notification comprises flagging the bend-compensated pressure computed using a moment fraction that is outside the established normal operating range.

21. A computer-readable medium storing a set of instructions which cause a processor of a sensor system to:
measure a first signal produced by a first transducer, the first signal having an associated first response to pressure and bending applied to a sensor module comprising the first transducer and a second transducer,
measure a second signal produced by the second transducer, the second signal having an associated second response to pressure and bending applied to the sensor module;
compute a moment fraction in response to the first signal and the second signal; and
generate a notification in response to the moment fraction.

22. The system of claim 21, wherein the instructions cause the processor to compute the moment fraction as a ratio of the bending moment applied to the sensor module to a predetermined maximum bending moment.

23. The system of claim 21, wherein the instructions cause the processor to compute the moment fraction as a fractional measure of the bending applied to the sensor module.

24. The system of claim 21, wherein the instructions cause the processor to compute the moment fraction as a relative change of duty cycles measured during an applied bend from duty cycles measured at a zero bending moment.

* * * * *